United States Patent [19]
Duske et al.

[11] Patent Number: 4,558,525
[45] Date of Patent: Dec. 17, 1985

[54] DEHYDRATION EQUIPMENT

[75] Inventors: Wilfried P. Duske, Milwaukee; Lowell C. Frank, Okauchee, both of Wis.

[73] Assignee: Progressive Development Incorporated, Milwaukee, Wis.

[21] Appl. No.: 221,433

[22] Filed: Dec. 30, 1980

Related U.S. Application Data

[63] Continuation of Ser. No. 53,973, Jul. 2, 1979, abandoned.

[51] Int. Cl.$^4$ .............................................. F26B 11/04
[52] U.S. Cl. ......................................... 34/128; 34/136
[58] Field of Search ........................ 34/128, 130, 136; 432/105

[56] References Cited

U.S. PATENT DOCUMENTS

| 742,265 | 10/1903 | Wentz | 34/128 |
| 2,132,972 | 10/1938 | Schmidt | 34/136 X |
| 2,683,594 | 7/1934 | Martenson et al. | 34/128 X |

FOREIGN PATENT DOCUMENTS

| 347455 | 1/1922 | Fed. Rep. of Germany | 34/128 |
| 44284 | 8/1927 | Norway | 34/128 |

*Primary Examiner*—Harold Joyce

*Attorney, Agent, or Firm*—Andrus, Sceales, Starke & Sawall

[57] ABSTRACT

A rotary drying system for particulate material includes a rotary dryer of the multiple pass drum construction with a horizontal axis of rotation. A furnace is coupled to one end and a horizontally disposed centrifugal separator of the scroll type is coupled to the opposite end. A small cyclone separator is coupled to the scroll separator and connected in a closed loop system with the scroll separator for continuous recycling air therethrough. The rotary dryer has essentially the largest vertical dimension and therefore the profile of the system is minimized. The rotary dryer is formed with an inner cylinder of a conical taper with a relatively small inlet end and progressively increasing passageway diameter to a large discharge end coupled to an intermediate passageway between the inner cylinder and an intermediate constant diameter cylinder. The intermediate passageway continuously expands in cross-section to a final discharge passageway formed by an outer concentric cylinder. Replaceable wear plate units support one end of the intermediate and inner cylinders for limited relative movement. The passageways are proportioned to establish a volumetric distribution for optimum drying characteristic and temperature drop to prevent product degradation and to produce efficient drying.

15 Claims, 7 Drawing Figures

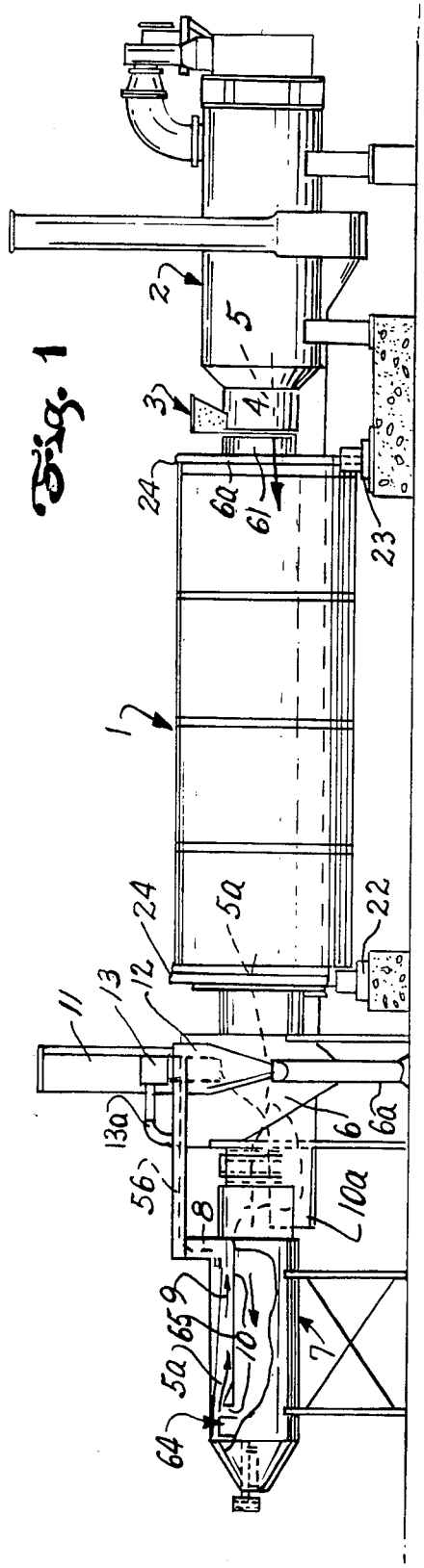
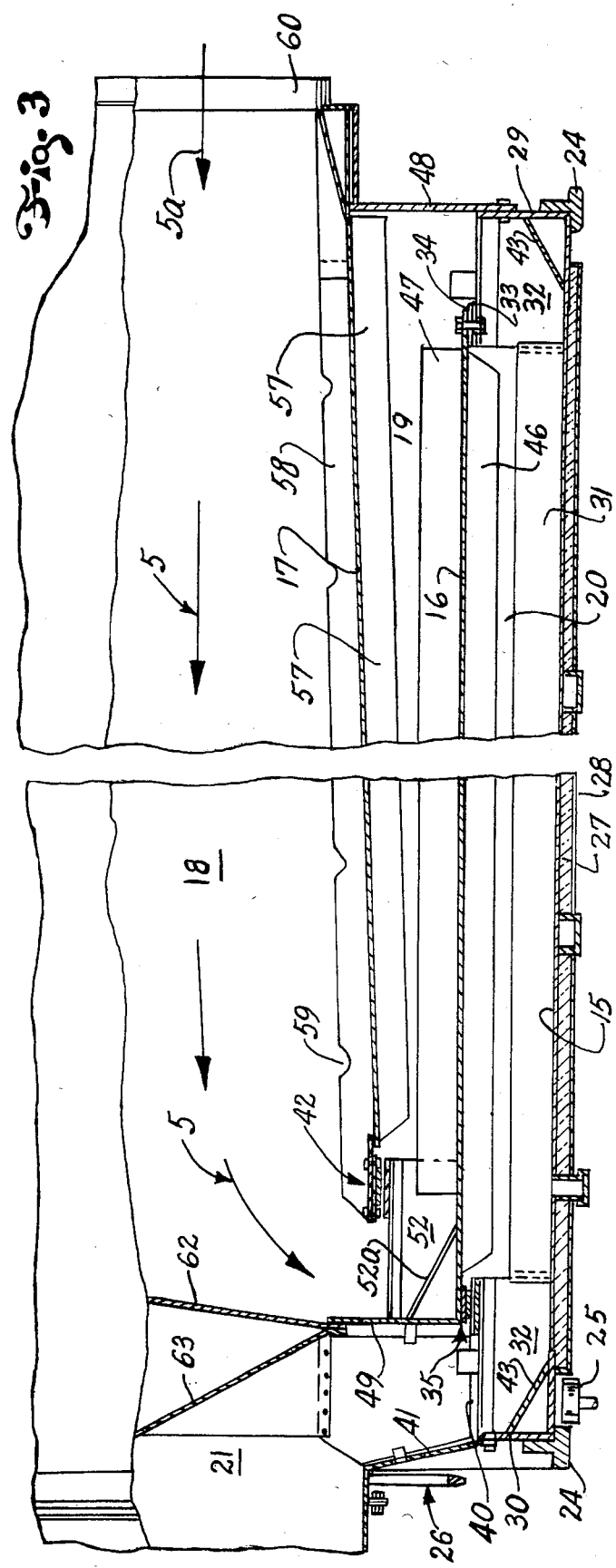

4,558,525

DEHYDRATION EQUIPMENT

This is a continuation application, of application Ser. No. 053,973, filed July 2, 1979 now abandoned.

BACKGROUND OF THE INVENTION

This invention relates to a dehydration apparatus in which particulate material is carried by a fluid medium through a rotary dryer.

Particulate matter which includes moisture or the other gaseous material may be passed through a rotary dryer for removal of the liquid or gaseous medium with subsequent separation of the particles from the fluid medium. Generally, in a rotary dryer system which is widely employed in industry and agricultural product drying and the like includes a gas or oil fired furnace or other heat source mounted to one end of a horizontally located and supported rotary dryer to supply hot air which is mixed with the product and through which particulate laden air is passed. The dryer includes a plurality of concentric cylinders or drums defining a central inlet passageway connected at one end to the hot air and connected in series by one or more intermediate passageways to an outermost discharge passageway. The particulate laden air moves through the multiple passageways by suction created by a dryer discharge fan. The rotary cylinders include suitable surface vanes to continuously circulate the particulate matter within the drums to the top portion and establish intimate mixing of the particles with the hot air or gases from the heat source. The air with the dried particle is fed to one or more cyclone separators, drop-out boxes or other suitable means for the separation of the dust particles from the hot gases. A cyclone separator generally includes a large vertically oriented unit having a top cylindrical inlet portion with a conical bottom discharge portion as well as a central top air exhaust duct member. The particulate laden air is fed into the unit with a centrifugal motion such as that as it moves downwardly through the cylindrical portion the particles are concentrated in the outer layer, and continue to drop downwardly through the cone-shape portion for exiting from the bottom. The primary carrier air is drawn upwardly through the center duct to the top of the cyclonic separator for further treatment or exhausting. For example, the air may be recirculated to the furnace. Alternately, a series of cyclonic separators may be provided to further clean the carrier air if it is to be exhausted to the atmosphere. Such rotary dryers are widely employed in connection with many industrial and agricultural products. Generally appropriate housing of the system apparatus includes enclosure of the furnace and dryer with the cyclonic separator mounted on or in a support structure.

Such systems are well known and are furnished by various sources of manufacture. Generally, the prior art has followed a basic pattern for years in which three constant diameter concentric cylinders are interconnected to define a triple pass drying flow path.

Although they provide satisfactory results, they do not provide necessarily the proper degree of drying which is often desired and/or required. Further, in various application scorching or excessive drying of particulate may occur. This is known to be particularly troublesome in connection with certain high sugar content wood products where scorching occurs as well as products or the like where various sized particles are encountered and degradation of product quality may occur if proper drying is not provided. Although various systems have been suggested a totally acceptable solution has not been found prior to the present invention.

SUMMARY OF THE PRESENT INVENTION

The present invention is particularly directed to a rotary dryer system employing an improved rotary dryer construction which may produce a significantly improved quality product and operate with significantly improved efficiencies as well as providing a total operating system which can eliminate the large bulky vertically oriented cyclonic separator.

Generally in accordance with the present invention, a multiple cylinder rotary dryer apparatus is formed with an inner tapered cylindrical wall means which preferably is of a substantially conical construction and having a relatively small inlet diameter means. The inner cylindrical means progressively increases in diameter, preferably in the manner of a conical member to a relatively large discharge diameter means, which is coupled by a transfer passageway to a return passageway along the exterior of the cylindrical means and an intermediate cylindrical means. The intermediate cylindrical means may be a cylinder having a constant diameter, thus creating a relatively small inlet portion adjacent the discharge of the inner cylindrical wall means and a relatively large discharge end adjacent the discharge end of the intermediate cylindrical wall means. Thus, a second continuously expanding flow path is again created for the particulate laden gases. The several wall means are in accordance known practice provided with suitable flights for carrying and recirculation of particulate material to the top portion of the cylinders from which the particulate tend to fall downwardly through the hot gases. A tapered construction with a smooth and progressively changing diameters has been found to provide a highly effective means of maximizing the contact time particularly of the heavier moisture laden particles.

Further, the passageways are proportioned to establish the volumetric distribution which results in an optimum drying characteristic, and particularly effective drying of the particulate material without scorching thereof or otherwise creating degradation of the quality of the dried materials. Generally, the intermediate passageway is enlarged while the outer passageway is reduced in volume. The resident time in the inner and intermediate passageways are optimized while the velocity in the final or discharge passageway is increased to minimize the problems heretofore resulting from excessive temperatures and particle-to-surface engagement, particularly at the area immediately adjacent the final discharge area from the rotary dryer. Thus, the present invention may employ a higher initial temperature than generally employed in comparable prior art systems, and in particular for drying of alfalfa and like material, initial inlet temperature may be 2100 degrees Fahrenheit with a discharge temperature on the order of 240 degrees Fahrenheit or less.

In such multiple pass drums, the several cylinders or drums are interconnected to each other for simultaneous rotation. However, the temperature variation from passageway to passageway is such that the cylinders tend to move relative to each other. Such movement has been accommodated by allowing one end of the cylinders to move relative to the adjacent cylinders.

Although necessary, such structure has also resulted in periodic maintenance requirement as the result of surface wear at the relatively moving interfaces. The cylinders in the preferred embodiment of this invention include replaceable wear means which minimize the cost of maintenance while producing an improved operational system.

Further, the present invention, which promotes the effective drying of the particles, has been used with scroll-type centrifugal separators rather than the standard or conventional cyclonic separator with separate fan. For example, in a particular unique embodiment of the present invention, a horizontally disposed centrifugal separator of the scroll-type is used with a horizontal flow pattern. This permits a construction of a dryer system in which the dryer drum has essentially the largest vertical dimension and therefore profile of the system minimized. This is particularly advantageous both from the standpoint of original cost and subsequent maintenance or service costs as well as appearance. The minimized profile is also advantageous where the system is housed in a conventional building as it avoids the necessity of the unusual building, height, or special roof openings, required with the usual cyclonic type separator and the like.

The present invention thus provides an improved rotary dryer apparatus for the efficient drying of material without scorching or excessive drying of the particles with a minimum space requirement.

BRIEF DESCRIPTION OF THE DRAWING FIGURES

The drawings furnished herewith illustrate a preferred construction of the present invention in which the above advantages and features are clearly disclosed as well as others which will be readily understood from the following description.

In the drawings

FIG. 1 is a side elevation view of a rotary drying system constructed in accordance with the present invention;

FIG. 3 is an enlarged fragmentary longitudinal section through the dryer illustrated in FIG. 1 and more fully and clearly illustrating the construction of a preferred embodiment of the present invention;

DESCRIPTION OF THE ILLUSTRATED EMBODIMENT

Figure 2:
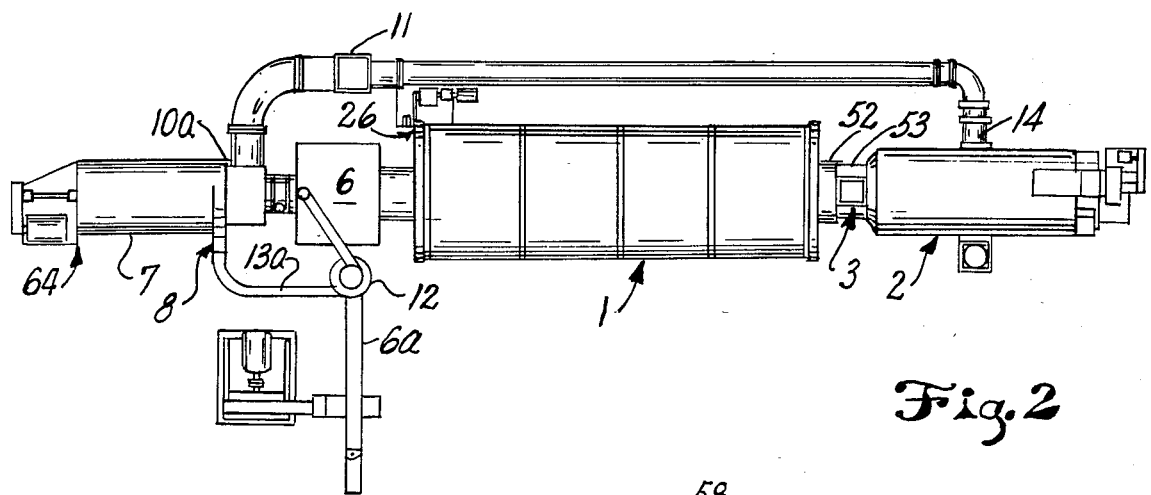
FIG. 2 is a plan view of the system shown in FIG. 1.

Referring to the drawings and particularly to FIG. 1, a rotary dryer system is illustrated constructed in accordance with the teaching of the present invention. Generally, the system includes a rotary dryer 1 which is mounted for continuous rotation about a longitudinal horizontal axis. A furnace 2 is secured to the inlet end of the rotary dryer 1 in combination with a particle material inlet section 3 for introducing of a moisture laden particles 4 or the like with hot drying gases 5 from the furnace into the inlet end of the rotary dryer 1. The particle laden gases 5 pass through dryer 1 and are discharged from the opposite end with the particles 4 essentially dry. The dry particle laden air 5a is passed through drop-out box unit 6 where the heavier particles drop out of the air carrier onto a suitable receiver 6a such as a screw-type conveyor 6a. The fine particle laden air 5a continues into a particle separator 7 forming part of a closed loop system in which the dried finer particles 4 are removed from the air 5a. As illustrated in FIG. 1, separator 7 is a cylindrical unit which is preferably mounted on a horizontal axis. The separator 7 may be a scroll-type centrifugal separator in which the particle laden air 5a moves axially through the unit 7 and then in a counterflow direction adjacent to the outer surface of the inner passageway, with a skimming discharge unit 8 removing the peripheral air layer within which the particles 4 are concentrated as at 9 and the clean air 10 exiting from the central portion through a discharge unit 10a to a conventional stack 11. The dust laden air 6a from separator 7 is further processed in a small cyclone separator 12.

The cyclone separator 12 as illustrated is of relatively small size compared to the usual cyclone separator used as a primary particle separator in rotary dryer systems. If the air handling volume of one cyclone separator 12 is not adequate, a plurality of the small cyclone separators may be connected in parallel. The cyclone separators 12 is a well known device operating on a centrifugal principle wherein the dust laden air 5b is introduced tangentially into the upper portion to establish a downward spiral flow toward and into a cone-shaped bottom portion which is open at the bottom. The particles 4 concentrate in the peripheral air layer and move downwardly through the upper portion. The air carrier exhausts upwardly through a central outlet duct 13 while the heavier particles 4 drop under the force of gravity through the bottom cone portion of the separator and from the bottom opening onto a suitable receiver such as the screw-type 6a conveyor or the like located to receive the particles 4 from drop-out box. The exhaust air from the cyclone separator 12 is returned directly from the top of the separator to the dropout box 6 via a suitable duct 13a and is recycled therefrom as a part of the carrier air into the scroll separator 7 to maintain the continuous and closed loop system. The recycled air is a small percentage of the total air through the separator 7 and adjustment of the cyclonic separator exhaust, such as usually provided, does not adversely effect the upstream pressure conditions such as may occur with the usual primary cyclonic separator systems. In the illustrated embodiment of the invention, the only exhaust air to atmosphere is the primary air from the scroll separator 7 and/or the exhaust from a vent and recycle stack of the furnace. Thus, the primary exhaust air from the separator 7 is coupled to the exhaust stack 11, and to furnace vent and recycle box 14 on the furnace 2. Thus the clean air may be wholly or in part recycled to the furnace.

The illustrated separator 12 is relatively small and clearly distinguished from the more conventional cyclone separator which has been and is widely employed as a primary particle separator in connection with the drying of grain and the like. Although such a prior art separator could be employed, effective primary separation requires large cyclone chamber construction and particularly a height substantially greater than the height of the rotary dryer 1 and associated equipment such as the furnace, the drop-out box, the secondary cyclone separators and the like, and often the primary cyclone separator is twice the height of the dryer. The present minimal profile assembly has distinctive advantages not only from original cost consideration construction but from the continuing maintenance and servicing considerations.

Thus, the present invention permits the construction of the total overall system as illustrated in FIG. 1 as an in-line system where the rotary dryer 1 essentially has the greatest vertical height and establishes the maximum overall profile of the system, while establishing effective separation of particulate matter from the air carrier. The minimal vertical height may be of particular significance in application requiring enclosure of the drying system. Thus, with the illustrated embodiment, only roof openings required is that for the exhaust air and the like. In prior art systems, the building must be exceptionally high or separate openings and/or construction provided to accomodate the large primary cyclone type separator.

The present invention is thus particularly directed to the rotary dryer 1 as well as the system which permits exiting through a simple vertical stack arrangement such that a minimized profile system can be provided.

The several elements other than the rotary dryer 1 may therefore be of any suitable or desired construction. The scroll separator 7 as shown and as described hereinafter is preferably constructed in accordance with the teaching of applicants' copending application entitled, "Fluid Borne Particulate Separator" and which was filed on even date with this application. The furnace may be of any well known construction but is preferably formed of a modular type construction illustrated to permit the convenience sizing of the furnace to installation. Thus, as previously noted for drying of alfalfa and the like an inlet temperature on the order of 2100 degrees Fahrenheit may be desired. For drying of bone meal and the like, the initial temperature may be as low as 700 or 800 degrees Fahrenheit. Similarly with wood grain products and the like, various other temperatures may be required. Such detail is readily understood by those skilled in the art and no further description thereof is given.

Figure 4:
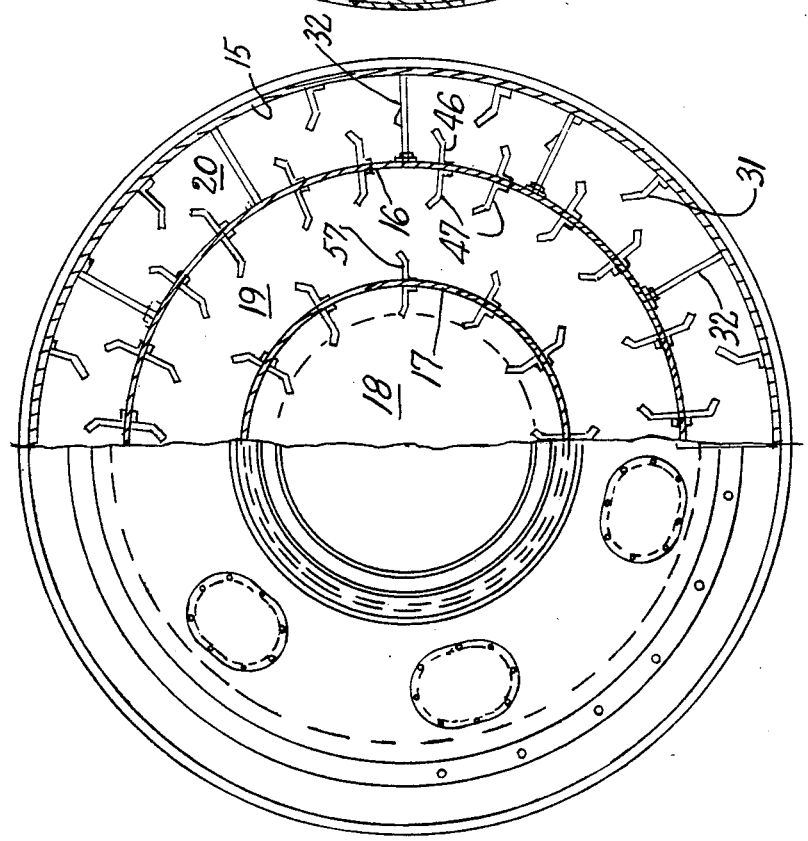
FIG. 4 is an end view with parts broken away and sectioned from the hot air entrance end of the rotary dryer.

More particularly, in the illustrated embodiment which is more clearly shown in FIGS. 2–4, the rotary dryer apparatus 1 is a multiple cylinder unit consisting of an outer drum or cylinder 15, on intermediate drum or cylinder 16 and a special inner drum or cylinder 17 which define a continuous flow path for the particle laden air 5. The inner cylinder 17 defines a central passageway 18 which extends from the furnace end of dryer 1 and which is joined to an intermediate return passageway 19 between cylinders 16 and 17. Passageway 19 is similarly joined to a final outer passageway 20 between cylinders 15 and 16. Passageway 20 terminates in an axial discharge passageway 21 opposite the inlet end of the dryer 1.

The several cylinders 15–17 are connected to rotate as a unit on a pair of supports 22 and 23 for the outermost cylinder 15. The supports may be suitable wheeled support of a suitable rotary pillow-type block.

As shown in FIG. 3, the outer cylinder 15 is provided with suitable end support rings 24 for vertical rotating support of the rotary drum. Suitable axial thrust rolls 25 are supported adjacent the inner faces of the one end ring 24. The rotary drum assembly is motor driven through a known chain and sprocket drive 26 secured to the discharge end of the rotary dryer 1, and particularly to the outer cylinder 15.

Figure 5:
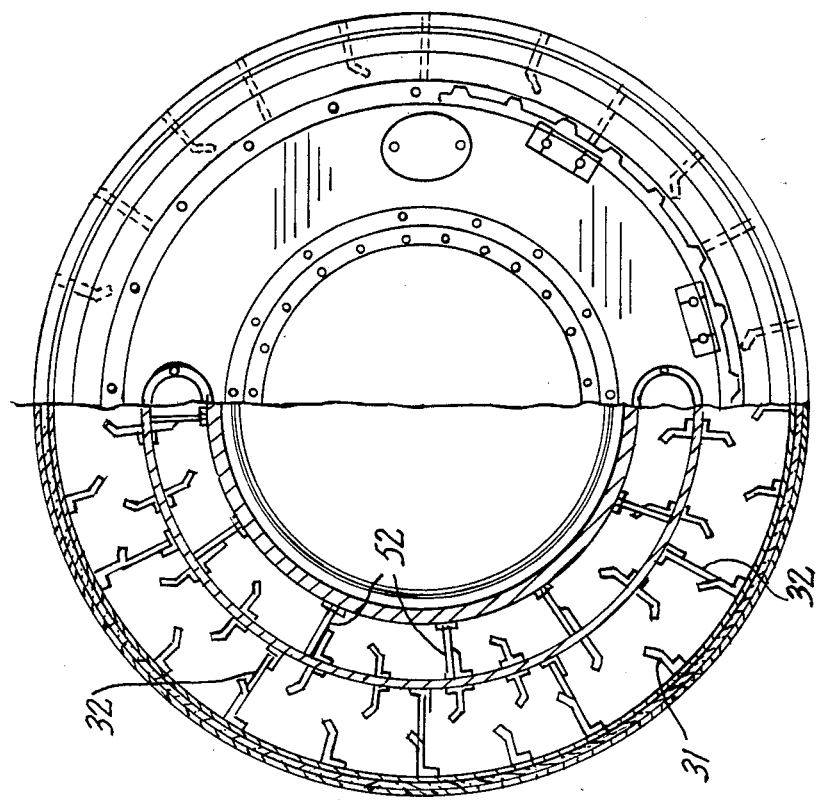
FIG. 5 is an end view with parts broken away and sections taken from the discharge end of the rotary dryer shown in FIGS. 1-3.

More particularly, the outer cylinder 15 is formed with a suitable outer insulating shell 27 in combination with an outer physical cover 28 to enclose and protect the high temperature insulation. The insulation 27 is spaced inwardly from the outermost ends of the outer cylinder 15 to expose the bearing support area of cylinder 15 for the thrust rolls 25. The outer cylinder 15 is formed with integral partial end walls 29 and 30 which project radially inwardly from the end guide rings 24 essentially for the depth of the final discharge passageway 20 and define the opposite end walls thereof. As shown in FIGS. 4–5, a plurality of circumferentially distributed and longitudinal flights 31 are secured to the interface of the outer cylinder 15 and project radially inwardly to slightly less than one half the depth of the passageway 20. A single one of the flights 31 as well as all other flights hereinafter described, is shown in FIG. 2 for clarity of illustration of the construction of the cylindrical wall and support means forming the several passageways. As shown in FIG. 3 flights 31 extend throughout the substantial central portion of the cylinder 15 and terminate at the opposite ends in spaced relation to the cylinder end walls 29 and 30. The inner wall of the outer passageway 20 is defined by the intermediate cylinder 16 which is concentrically mounted on the common axis for all members 15–17 to define an annular passageway 20. A plurality of circumferentially distributed intermediate cylinder support brackets 32 are secured within the opposite ends of the outer cylinder 15. The brackets 32 extend inwardly from the opposite ends of the end walls 29 and 30 beneath the ends of cylinder 16. The brackets 32 adjacent the inlet end 29 of the dryer 1 includes a flanged top wall to which a plurality of support plates 33 are secured. A suitable support ring 34 is secured to ends of cylinder 16, and the total assembly is bolted together such that the end of cylinder 16 is firmly attached to the cylinder 15 at the transfer location at the end 29. Plates 33 may be a suitable relatively short plate welded or otherwise secured, one each to each of the brackets 32. The ring 34 may be a continuous ring secured to the outer face of cylinder 16. The cylinder 16 extends from the attachment means 33–34 with the opposite end overlying the brackets 32 adjacent the discharge end of the dryer 1 and mounted with suitable replaceable sliding support means. The brackets 32 are top-flanged members with a replaceable wear plate means 35 bolted thereto and defining a sliding support. The intermediate cylinder 16 is affixed to the outer cylinder by a bolted interconnection immediately adjacent to the inlet end of the dryer, while the opposite ends of the cylinder 16 is allowed to move relative to the outer cylinder 15.

Figure 6:
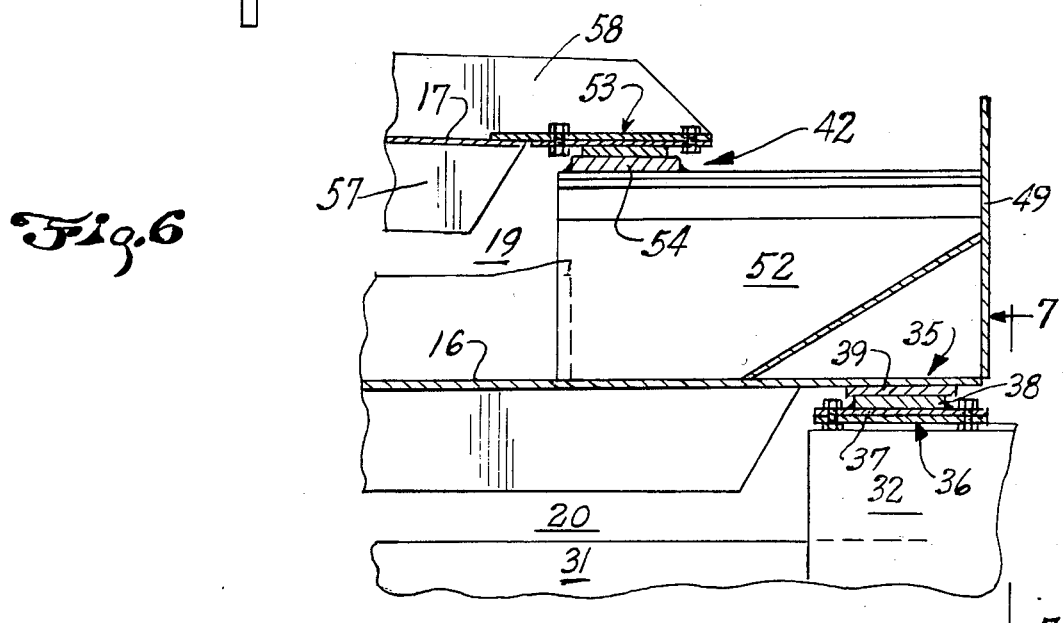
FIG. 6 is an enlarged fragmentary view of a portion of FIG. 3 illustrating a sliding support for a drum cylinder.
Figure 7:
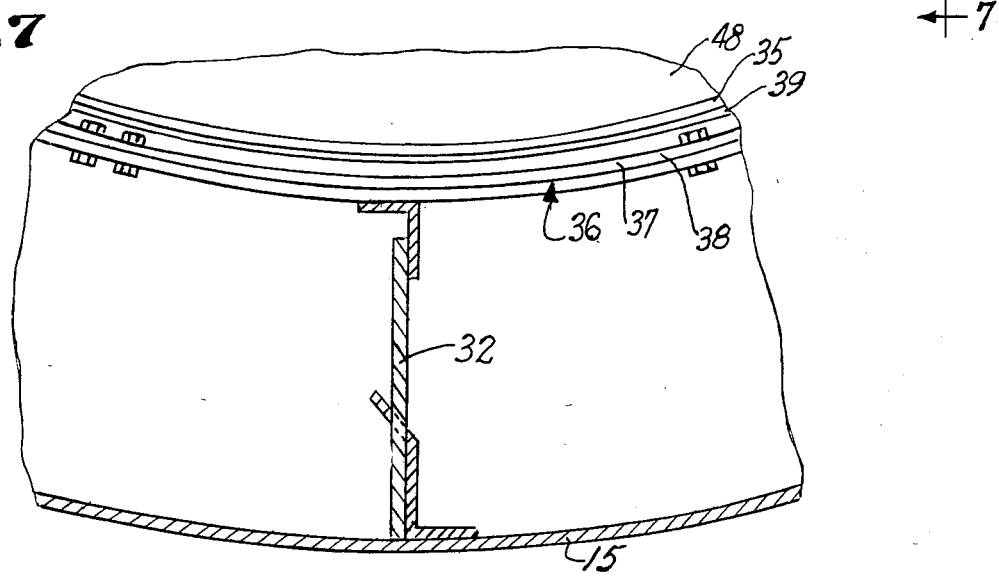
FIG. 7 is a sectional view taken on line 7—7 of FIG. 6.

As shown most clearly in FIG. 6, replaceable wear means 35 includes a supporting segmented wear ring 36 which is releasably affixed to tops of the end of the circumferentially distributed end brackets 32. The wear ring 36 is formed of a plurality of similar segments to permit individual replacement of each segment. Each of the wear plate segments includes a circumferential mounting base 37 which is provided with bolt openings appropriately aligned with bolt openings in the tops of the several brackets 32 for bolting of the wear plate segments into position. A wear plate 38 is welded or otherwise secured to the mounting base 37. Each plate 38 extends circumferentially into abutting engagement with the adjacent plates 38. In the illustrated embodiment of the invention, the segments define a continuous wear surface, with each segment spanning 60 degrees and six segments provided to define 360 degrees wear surface.

The adjacent portion of the intermediate cylinder 16 is provided with an outer support ring 39. The ring 39 is a continuous ring member which is welded or otherwise firmly affixed to the outer periphery of the intermediate cylinder 16 in alignment with the wearplate 38. The axial length of ring 39 is greater than that of the wear plate 38 and ring 39 is located to extend beyond the opposite ends of wear plate 38 at least by the distance of relative movement during the normal operation of the rotary dryer 1. The wear ring 39 is also formed of a relatively hardened material, with the outer face finished to establish a smooth sliding surface to the shorter wear plate 38. During the relative movement between the intermediate cylinder 16 and its support bracket 32 wear created will be on the smaller length of the wear plate 38. As a result, a continuous and relatively smooth interface support engagement is maintained.

If one or more of the wear plate 38 is excessively worn, that unit may be readily replaced by removal of a dryer end wall structure to permit access to the drum structure and particularly the cylinder support structure 32. The worn wear plate unit 35 is readily replaced by unbolting and withdrawal of the worn section.

In the illustrated embodiment, intermediate cylinder 16 terminates generally in spaced relation to the end wall 30 of the outer cylinder 15 to define an exit passageway 40 into the exhaust passageway unit 21 from the outermost dryer passageway 20. The end wall of the exit passageway 40 includes one or more removable end wall sections 41 which permit access to the ends of cylinder 16 and 17 to permit access to the replaceable wear means 35. A similar wear means 42 for cylinder 17 is subsequently described.

In the illustrated embodiment of the invention, similar cone plates 43 are show in FIG. 3 secured in the corner of the entrance and exit ends of the outer cylinder 15 to assist the product flow into and from the passageway 20 and finally into discharge duct unit 21.

The opposite end of cylinder 16 is similarly spaced from end wall 29 to define a transfer passageway from passageway 19 to passageway 20 and supported on the brackets 32 adjacent wall 29. The securement is a fixed attachment with appropriate support rings 33 and 34 secured to the cylinder 16 and to brackets 32 with suitable attachment bolts provided at each bracket.

The intermediate cylinder 16 is shown as a cylindrical member of constant diameter having flight 46 secured to its outer surface and extending essentially coextensive with the corresponding flights 31 of the outer cylinder 15. Flights 46 are offset by one half the distance between flights 31. In addition, similar inner flights 47 are secured to the inner face of the intermediate cylinder 16 and extend from the transfer passageway portion with the opposite end spaced axially inwardly of the opposite end of cylinder 1t. The opposite ends of intermediate passageway 19 are closed by suitable end walls 48 and 49 which with the inner cylinder 17 form passageway 19. End wall 48 is secured to wall 29 and extends radially inwardly and is welded or otherwise secured to the inner cylinder 17 and supports the cylinder 17. End wall 49 is secured to the opposite end of cylinder 16. A plurality of support brackets 52 are secured to the end wall 49 and extend inwardly beneath the inner cylinder 17, which is spaced from the end wall 49 to form and define a transfer passageway for the air and particles flowing from the central or inner passageway 18 to the intermediate passageway 19. Suitable cone plates 52a at the transfer passage may again be provided for effective turning of the air from the inner passageway 18 into the intermediate passageway 19. The sliding support and wear means 42 is secured to the brackets 52 and inner cylinder 17 to slidably support the cylinder 17. Thus, wear means 42 includes a segmented wear plate unit 53 secured to the outer face of cylinder 17 and a hardened wear ring 54, of greater axial length than the wear plate of unit 53, welded or otherwise secured to brackets 52. The wear means 42 is thus essentially the same as wear means 35 with the parts reversely mounted.

The inner cylinder 17 is specially constructed as a generally continuously tapered member and preferably as a conically shaped member having the inner end slidably supported on the end brackets 52 in spaced relation to the end wall 49 to define the transfer passageway. The inner cylinder 17 extends axially and radially from such large diameter inner end to a small diameter inlet end, with the outermost end fixedly supported by the end wall 48 upon the wall 29. Circumferentially distributed flights 57 are secured to the exterior face of the inner cylinder 17 and extend from the transfer passageway to the opposite end wall and thus through the intermediate passageway 19. Flights 57 are offset circumferentially to the center of the flights 47 on the interior of cylinder 16.

Inner flights 58 are secured to the inner face of the conical inner cylinder 17. Flights 58 are shown as continuous with longitudinally spaced notches 59 along the length thereof to accommodate thermal expansion. Each flight may be formed of a series of short spaced flights with alternate rows overlapping.

The inlet end of the conical inner cylinder 17 is fixedly attached to an annular outer couplimg member 60 which projects outwardly into a tubular discharge member 61 of the adjacent heat source and particle mixing inlet section 5.

The discharge passageway unit 21 is formed to the opposite end of the inlet cylinder 17 and includes an end closure wall 62 with a generally cone-shaped cross-section for directing of the air from the central cylindrical passageway 18 into the transfer passages to passageway 19.

The discharge passageway 21 on the opposite side of wall 62 preferably includes an outer end wall 63 for directing of the dry particle laden air 59 outwardly into the discharge duct work for the transfer to the drop-out box and then centrifugal separator 7.

The separator 7 as illustrated is a fandriven unit having a fan wheel unit 64 adapted to establish a suction pressure through the upstream portion of the system and particularly at the furnace 2. Thus fan unit 64 constitutes the total air moving power source for the system for rapid movement of the particle borne air 5 from the furnace 2, through the rotary dryer 1 as well as the separator 7 and cyclone separator 12. Additional secondary fan systems may of course be supplied but are generally not required depending upon the particular installation. The separator 7 may of course be of any suitable construction. A particularly advantageous construction is shown in the previously identified copending application of the applicants. As more fully disclosed therein, a scroll type separator includes a central axially extended air duct 65 to the fan wheel assembly 64. The air flows thru and then reverses its direction into an outer passageway between the duct 65 and an outer cone-shaped duct 66. The fan unit 64 imparts a centrifugal motion to the particle laden air resulting in a spiral flow of the air back through the outer discharge passageway. The heavily particle laden air is concentrated in the outer layer and withdrawn through the skimmer discharge unit 13 while the relatively clean air is discharged into an exhaust stack 11 for exhausting from the building or return for recycle.

In operation the system operates basically in accordance with known functioning, wherein the furnace 2 provides appropriate heated air which is mixed with moist particulate matter and drawn inwardly into dryer 1 and particularly cylinder 17 to generate the air stream 6 for carrying of the particulate material in and through the multiple cylinders passageways 18–20. The conically-shaped inner cylinder 17 results in an increased air velocity at the cylinder inlet and a reduced air velocity at the end of the inner cylinder outlet. The cylinder 17 with the constant diameter cylinder 16 results in a similar passage 19, with volume throughout the length of the passageways increased. This provides more effective resident time of the particulate matter 4 in the inner and intermediate passageways 18 and 19 where the hottest air exists. Conversely, with the illustrated arrangement and the outer passageway 20 may be reduced in volume proportionately to maintain the desired product flow.

Conical inner cylinder 17 with the increased air velocity at the inlet end functions to increase the rate of separation of the smaller and/or dryer particles from the larger and/or more moist particles. Further, the arrangement tends to convey the dryer particles into the colder temperature region. The system thus particularly increases the wet product resident time within the highest temperature region of passageways 18 and 19.

The conical or progressively changing diameter inner cylinder also establishes a higher gradient in the temperature versus length along the length of the inner cylinder. The taper from the inner end to the outlet also assists in the movement of the particles and this reduces the load of the hot fluid carrier.

Thus, movement of the particulate laden air through the system results in an optimum distribution of the particulate material in relationship to the temperatures. The relatively small inlet results in a relatively high inlet velocity which progressively decreases as the particle laden air moves through the progressively enlarging inner cylinder to the discharge end, where it flows about the end of the cylinder and moves in a counterflow direction through the intermediate passageway. This passageway again defines a progressively increasing volumetric chamber with a consequent similar flow characteristic and a corresponding maximum resident time of the particulate matter until the material reaches the discharge end of the intermediate passageway 19 where the direction is again reversed for final passage through the outer passageway. In accordance with an optimum construction, the relative volumetric proportions are varied from that which is generally employed in the art. Generally, in accordance with the teachings of the inventors, the outermost passageway 20 is of a reduced volume and cross-section while the intermediate passageway 19 is increased to optimize the resident time of the relatively moist particles in the highest temperature passageways while increasing the velocity and therefore decreasing the resident time in the relatively low temperature outer passageway 20. This not only provides for optimum time within the various passageways but results in an optimum support of the dryer particles in the final passageway 20. Thus, generally it is well known that a greatest proportion of the drying occurs within the innermost passageways and generally may be as high as 60 percent of the total drying affect. Once again the intermediate passageway may affect drying on the order of 25 percent while the final passageway affects a final drying of the last 15 percent level of the total drying affect. This has various distinct advantages where the system is properly proportioned. For example, in a practical application for the drying of alfalfa, the inlet temperature may be and has been selected as 2100 degrees Fahrenheit. The expanding tapered cylinder 17 associated with the present invention results in more evaporative cooling of the particles and a decrease in the temperature to the order of 600 degrees Fahrenheit at the exit end of the inlet cylinder 17. Further cooling occurs in passageways 18 and 20 with a discharge temperature substantially below 240 degrees Fahrenheit and in a practical application generally of the order of 250 degrees Fahrenheit. The temperature in the first cross over or transfer passageway from inner passageway 18 to intermediate passageway 19 is thus on the order of 600 degrees Fahrenheit while the discharge temperature is approximately 230 degrees Fahrenheit. As a result, the temperature on the opposite sides of the intermediate cylinder 16 adjacent to the discharge passageway 21 will be at approximately the average of these two temperatures, namely 600 plus 230 divided by 2 or approximately 415 degrees Fahrenheit. This is significantly smaller than the average temperature in conventional triple pass dryers. The temperature of the intermediate wall 16 at the discharge or drum outlet is therefore correspondingly reduced in temperature. This is the location where the particles may come to rest on the exterior of cylinder 16 before the particles exit the dryer. Thus, as the dried particles move through the final discharge passageway, and in fact repeatedly come to rest on the exterior surface of the intermediate cylinder just prior to discharge. The particles at this point very closely approach the desired final moisture content and therefore do not have any affective evaporative cooling. If the drum or cylinder temperature is above a certain level, discoloration of the particles, if not charring or other product degradation may result. For example, when drying of wood flakes or the like, significant discoloration of the dried product and a "blue haze" condition is often created in the usual triple pass dryer because of the temperature distribution. Similarly, in drying alfalfa, the dried product has lost much of its color during the drying process. This is true even though the starting temperature is often only 1600 degrees. The reduction in temperature associated with the present invention essentially prevents such discoloration and/or product quality degradation. For example, it has been found that in a practical implementation of the present invention, the dried product is visibly significantly improved when compared to a conventional three-pass constant diameter dryer such as widely used in the prior art from the inception of the triple pass drum design.

The high inlet temperature with the low outlet temperatures thus not only result in a superior quality product which is both readily analyzed from a technical standpoint but is also visibly apparent. The inlet/outlet temperature differential also indicates improved efficiency of operation with a maximum heat conversion in the drying process. Further, the total air volume supplied may be reduced because the product moves more readily thorughout the system as the result of the tapered construction. This facilitates use of the single fan section or blower system of the scroll separator such as previously described.

Similarly, similar efficiencies and product quality improvements were noted when the unique dryer apparatus is applied to other materials. For example, in the application of the present invention to a blood meal dryer with an usual operating temperature of the order of 700 to 800 degrees Fahrenheit, a significant improvement in the quality was obtained. Thus the protein level of the blood mean resulting from the processing through the rotary dryer of this invention was generally on the level of 93 percent. This is in contrast to a conventional constant diameter rotary dryer wherein the protein level of 85 percent is normally found as acceptable.

The air velocity in the outer reduced volume passageway 20 results in a slightly increased flow rate. The particles are relatively fully dried during this final flow through passageway 20 and the increased velocity results in a somewhat improved entrainment of the particles in the air and particularly the small dried particles. This holds the fine particles from the hottest temperature area and surfaces and minimized excessive particle drying, and particularly protects such particles from dehydration and breaking of the particles into pollutants.

Various modifications to the described structures may of course be provided. The intermediate drum may, for example, be tapered to further increase the cross-section, and provide an outer tapered passageway if the constant outer diameter cylinder is used. The surfaces adjacent the discharge area may also be provided with insulation to further minimize internal hot spots. Although the present invention is particularly useful in the tirple pass rotary dryer, other rotary dryers with more or less passageways may be constructed using a tapered inner cylinder. The reduced profile system could of course be constructed with a single pass rotary dryer. Further, although described as employing hot air as the carrier any other suitable fluid medium may of course be used. These and similar variations and modifications can be provided based on ordinary design and no further description is therefore given herein.

The inventors have found that an inner conically shaped cylinder be an essentially smoothe continuous surface to maintain the progressive change in the diameter of the wall to minimize particle entrainment and entrapment within the dryer.

Various modes in carrying out the invention are contemplated as being within the scope of the following claims, particularly pointing out and distinctly claiming the subject which is regarded as the inention.

We claim:

1. A concurrent flow rotating dryer apparatus, including a plurality of at least three generally cylindrical members mounted concentrically adjacent each other on a common axis of rotation and axially aligned and defining a series of interconnected axial passageways including a central inlet passageway means into an innermost central cylindrical member of said three generally cylindrical members, pressurizing means for introducing a particle laden fluid including particles to be dried into an inlet end of said central inlet passageway means under pressure and establishing a particle laden fluid stream with said particles entrained in said fluid stream passing axially from said inlet end back and forth through said series of interconnected axial passageways to an outermost passageway, said fluid serving to carry said entrained particles through said axial passageways as a result of the movement of the fluid stream, means for heating said fluid at said inlet end whereby said particles are subject to the highest temperature at said inlet end and to a progressively reducing temperature in passing through said passageways, means for exiting said fluid stream from said outermost passageway, said innermost central cylindrical member spaced radially inwardly of the adjacent cylindrical member and is a tapered member having a substantially tapered configuration defining a relatively small diameter open end adjacent the inlet end and a relatively large discharge open end with the highest temperature and velocity at the inlet end and defining a progressively increasing cross-section passageway in the direction of the movement of the fluid stream and of said particles whereby said particle laden fluid enters the inlet end at a substantially higher velocity and temperature than the fluid exits from the opposite discharge open end of the innermost central cylindrical member and wherein said fluid entrained particles drying is facilitated during the passing through said passageways, said tapered configuration controlling the resident time of the particles in the corresponding passageway to control the drying of the particles with a temperature drop per unit of length of the central cylindrical member increasing progressively in passing from the inlet to the outlet end of the innermost cylindrical member.

2. The apparatus of claim 1 wherein a second of said cylindrical members is of a constant diameter and said second of said cylindrical members is located adjacent said tapered member to define a progressively increasing flow passageway therebetween.

3. A concurrent flow rotating dryer apparatus including a plurality of at least three generally cylindrical members mounted concentrically and in axial alignment adjacent each other on a common axis of rotation and defining a series of interconnected axial passageways including a central passageway means, means for introducing a heated particle laden fluid under pressure into an inlet end of said central passageway means and thereby establishing a particle laden fluid stream passing from said inlet end axially back and forth through said series of axial passageways to an outermost passageway means, means for exiting said fluid from said outermost passageway means, the innermost cylindrical member defining said central passageway means and being spaced radially inwardly of the adjacent cylindrical member, said innermost cylindrical member having a substantially tapered configuration defining a relatively small diameter open end at said inlet end to receive the heated particle laden fluid stream and increasing progressively from said inlet end throughout the length of the innermost cylindrical member and moving said stream through an increasing diameter in said central passageway means to a relatively large diameter discharge end whereby said particle laden fluid enters the inlet end at a substantially higher velocity than at the exit end and said fluid carries said particles therewith with a progressively decreasing velocity and the particle laden fluid exits from the opposite discharge open end of the innermost cylindrical member at a substantially reduced velocity.

4. The apparatus of claim 3 wherein said tapered innermost cylindrical member is surrounded by an intermediate round cylindrical member of constant diameter.

5. The apparatus of claim 3 wherein said apparatus includes three cylindrical members defining three passageways.

6. The apparatus of claim 5 wherein said axial passageway includes an intermediate passageway means and said intermediate and outermost passageway means are proportioned substantially in the ratio to the innermost cylindrical member volume of one and one-half and of two and one-quarter.

7. The apparatus of claim 5 wherein said innermost passageway means increases in cross-sectional area by a factor of substantially $1\frac{1}{2}$, said intermediate passageway means increases in cross-sectional area by a factor of $1\frac{1}{2}$ and said outermost passageway means including a constant cross-sectional area substantially greater than the inlet opening by a factor of $2\frac{1}{2}$.

8. The apparatus of claim 3 including only three of said cylindrical members and including an intermediate constant diameter cylinder and an outer constant diameter cylinder, said cylinders being mounted on a common axis of rotation and offset to define coupling passageways between said axial passageways.

9. A concurrent flow rotary dryer having a triple pass flow pattern adapted to support a particle laden fluid stream for drying of the particles, comprising three concentric and axially aligned cylinders including an outer cylinder and an intermediate cylinder and an innermost tapered cylinder, said innermost tapered cylinder having a generally conical taper defining an inlet passageway from a small inlet end to a large discharge end and mounted coaxially of said outer and intermediate cylinders, rotary support means for supporting said three cylinders for rotation about the common axis, pressurizing means to introduce a heated particle laden air into said inlet end to create a particle laden air flow from the inlet end of the tapered cylinder and includes means for heating said air prior to the introduction into said tapered cylinder, said particles including moisture, said intermediate cylinder located intermediate the outer cylinder and the innermost tapered cylinder and concentrically of said outer cylinder and defining an intermediate passageway and an outer passageway, said innermost tapered cylinder having said large discharge end interconnected to said intermediate passageway by a transfer passageway for transferring the fluid from the inlet passageway formed by the innermost tapered cylinder and into the intermediate passageway, a transfer passageway between said intermediate passageway and said outer passageway adjacent the outlet end of the intermediate cylinder, and a discharge passageway means secured to the outer cylinder adjacent to the transfer passageway between the innermost tapered cylinder and the intermediate cylinder at the discharge end of the dryer, and said pressurized means and said heating means creating movement of said particle laden fluid stream through said passageways to progressively heat said particles to predetermine dry state where at least some of said particles engage the exterior of said intermediate cylinder at said discharge end.

10. The rotary dryer of claim 9 wherein said intermediate cylinder has a constant diameter and said intermediate passageway has an increasing cross-section from the inlet end to the discharge end.

11. The rotary dryer of claim 9 including means to establish an air temperature at the inlet end of the central cylinder of substantially 2100 degrees Fahrenheit, means for supplying product having 80 percent moisture content, said product being discharged with substantially 10 percent moisture content, and said air exiting at a temperature of less than 240 degrees Fahrenheit.

12. The rotary dryer of claim 9 wherein said temperature of said air is reduced to the order of 600 degree Fahrenheit at the transfer passageway between the inlet passageway and the intermediate passageway.

13. The apparatus of claim 9 wherein the cross-sectional mean area of the inlet to said passageways are with respect to the inner cylinder inlet in the ratio of 1, of 1.5 and of 2.5 to 1.

14. The apparatus of claim 9 wherein the inlet and intermediate passageway constitutes in excess of 50 percent of the total volume of the inlet, intermediate and outer passageways and the volume of said intermediate passageway is significantly greater than said inlet passageway.

15. The apparatus of claim 9 wherein said inlet passageway increases in cross-sectional area by a factor of substantially $1\frac{1}{2}$ and said outer discharge passage is constant substantially greater than the inlet opening by a factor of $2\frac{1}{2}$.

* * * * *

UNITED STATES PATENT AND TRADEMARK OFFICE
CERTIFICATE OF CORRECTION

PATENT NO. : 4,558,525
DATED : December 17, 1985
INVENTOR(S) : Wilfried P. Duske et al It is certified that error appears in the above-identified patent and that said Letters Patent is hereby corrected as shown below:

Col. 7, line 61, delete "1t" and substitute therefor ---17---; Col. 8, line 40, delete "couplimg" and substitute therefor ---coupling---; Col. 8, line 55, delete "fandriven" and substitute therefor ---fan-driven---; Col. 11, line 42, delete "tirple" and substitute therefor ---triple---; Col. 11, line 52, delete "smoothe" and substitute ---therefor ---smooth---; Col. 11, line 59, delete "inention" and substitute therefor ---invention---; Col. 14, line 30, delete "degree" and substitute therefor ---degrees---; Col. 14, line 45, after "said" insert ---intermediate passageway increases by a factor of 1 1/2 and said ---; Col. 14, line 46, after "stant" insert ---and---.

Signed and Sealed this

Twenty-fourth Day of June 1986

[SEAL]

*Attest:*

DONALD J. QUIGG

*Attesting Officer*  *Commissioner of Patents and Trademarks*